US008628758B2

(12) United States Patent
Ilekti et al.

(10) Patent No.: US 8,628,758 B2
(45) Date of Patent: Jan. 14, 2014

(54) PROCESS FOR MAKING UP THE LIPS

(75) Inventors: Philippe Ilekti, Maison-alfort (FR); Laure Le Chaux, L'hay les Roses (FR)

(73) Assignee: L'Oreal, Paris (FR)

( * ) Notice: Subject to any disclaimer, the term of this patent is extended or adjusted under 35 U.S.C. 154(b) by 310 days.

(21) Appl. No.: 12/921,479

(22) PCT Filed: Mar. 6, 2009

(86) PCT No.: PCT/IB2009/050944
§ 371 (c)(1),
(2), (4) Date: Oct. 14, 2010

(87) PCT Pub. No.: WO2009/112991
PCT Pub. Date: Sep. 17, 2009

(65) Prior Publication Data
US 2011/0038821 A1    Feb. 17, 2011

Related U.S. Application Data

(60) Provisional application No. 61/064,888, filed on Apr. 1, 2008.

(30) Foreign Application Priority Data

Mar. 13, 2008   (FR) .................................... 08 51643

(51) Int. Cl.
*A61Q 1/04*    (2006.01)
*A61Q 1/06*    (2006.01)

(52) U.S. Cl.
USPC ............................................ 424/64; 424/401

(58) Field of Classification Search
None
See application file for complete search history.

(56) References Cited

U.S. PATENT DOCUMENTS

| 4,717,720 A | 1/1988 | Shroot et al. |
| 4,740,519 A | 4/1988 | Shroot et al. |
| 4,920,140 A | 4/1990 | Shroot et al. |
| 4,925,658 A | 5/1990 | Shroot et al. |
| 4,940,696 A | 7/1990 | Shroot et al. |
| 5,098,895 A | 3/1992 | Shroot et al. |
| 5,750,723 A | 5/1998 | Eldin et al. |
| 5,847,156 A | 12/1998 | Eldin et al. |
| 5,935,584 A | 8/1999 | Guerrero et al. |
| 6,143,283 A * | 11/2000 | Calello et al. .................... 424/64 |
| 6,177,092 B1 | 1/2001 | Lentini et al. |
| 2002/0085982 A1* | 7/2002 | Dorf ................................ 424/63 |
| 2007/0141003 A1 | 6/2007 | Blin et al. |
| 2009/0202461 A1 | 8/2009 | Rodriguez et al. |

FOREIGN PATENT DOCUMENTS

| DE | 196 27 931 A1 | 1/1998 |
| EP | 0 199 636 A1 | 10/1986 |
| EP | 0 325 540 A1 | 7/1989 |
| EP | 0 402 072 A2 | 12/1990 |
| EP | 0 542 669 A1 | 5/1993 |
| EP | 0 787 730 A1 | 8/1997 |
| EP | 0 787 731 A2 | 8/1997 |
| FR | 2 570 377 A1 | 3/1986 |
| FR | 2 886 840 A1 | 12/2006 |
| JP | A-2-295912 | 12/1990 |
| WO | WO 96/08537 A1 | 3/1996 |
| WO | WO 00/26167 A1 | 5/2000 |
| WO | WO 2004/060332 A1 | 7/2004 |
| WO | WO 2007/078460 A2 | 7/2007 |

OTHER PUBLICATIONS

International Search Report dated Jul. 8, 2009 in corresponding International Application No. PCT/IB2009/050944.
Written Opinion of the International Searching Authority dated Jul. 8, 2009 in corresponding International Application No. PCT/IB2009/050944.

* cited by examiner

*Primary Examiner* — Jyothsna Venkat
(74) *Attorney, Agent, or Firm* — Oliff & Berridge, PLC

(57) ABSTRACT

The present invention relates to a process for making up the lips, comprising at least one step of placing in contact on the surface of said lips: —at least one water-soluble organic acid, —at least one alkali metal or alkaline-earth metal carbonate or bicarbonate, and —an aqueous medium, said organic acid and said carbonate or bicarbonate being present in different compositions.

19 Claims, No Drawings

PROCESS FOR MAKING UP THE LIPS

The present invention relates to a process for making up the lips that is capable of affording a novel makeup effect, said effect resulting from placing in contact in an aqueous medium, for instance saliva on the surface of the lips, at least one water-soluble organic acid and an alkali metal or alkaline-earth metal carbonate or bicarbonate.

In the field of lip makeup, the main expectation of lipstick users is a modification of the visual appearance of the lips, generally in terms of coloration, gloss and, increasingly often, volume. To obtain a volumizing effect or a fleshy effect, two alternatives are currently available to users. The first alternative involves recourse to cosmetic surgery and, with regard to its invasive nature, is therefore not adopted per se by the vast majority of users. The second alternative is directed toward affording this effect via the presence, in the film of makeup applied to the lips, of one or more materials capable of giving a suitable optical effect. For obvious reasons, such a volumizing effect is entirely artificial and is perceived as such visually. The current tendency increasingly encourages users to favor a makeup effect termed "natural", i.e. which has the resemblance of a natural lip flesh tone and/or volume.

Consequently, there is at the present time a need for a means of making up the lips that is capable of affording fleshy and color effects termed as being natural.

The aim of the present invention is, precisely, to meet this expectation.

More particularly, the invention relates to a process for making up the lips, comprising at least one step of placing in contact, on the surface of said lips:
- at least one water-soluble organic acid,
- at least one alkali metal or alkaline-earth metal carbonate or bicarbonate, and
- an aqueous medium.

According to a particularly advantageous embodiment, the organic acid and the carbonate or bicarbonate are present in different compositions.

For the purposes of the invention, this means that the two compositions comprising respectively the organic acid and the carbonate or bicarbonate are conditioned separately of each other.

The placing in contact of the organic acid and of the alkali metal or alkaline-earth metal carbonate or bicarbonate in the presence of water is conducive to generating an evolution of $CO_2$, which is the cause of an effervescence reaction. Against all expectation, the inventors have found that when this effervescent reaction takes place on the surface of the lips, it is reflected by a significant increase in the volume of the lips and an intensification of their natural flesh tone.

From a cosmetic viewpoint, document U.S. Pat. No. 6,177,092 describes a self-foaming skin-cleansing composition that is based on the principle of effervescence induced by the combination of an organic acid and sodium bicarbonate in the presence of water. In document U.S. Pat. No. 5,935,584, which concerns a skincare product, mention is also made of a combination of ascorbic acid and sodium bicarbonate; however, the latter is essentially used in order to modify the excessively acidic pH of the ascorbic acid. Finally, document WO 2007/078 460 concerns a skincare product in the form of an anhydrous facial mask, especially containing an acid and an alkali metal carbonate or bicarbonate, which, after application to the skin, has the property of being removed easily by virtue of its foaming power in the presence of water.

Consequently, to the inventors' knowledge, the advantageous effect in terms of lip makeup of the effervescence principle induced by the combination of an organic acid and an alkali metal or alkaline-earth metal carbonate or bicarbonate in aqueous medium has never been described.

The makeup process according to the invention advantageously generates a smooth, bubbly effect that is visible on the lips and, moreover, slight tingling of the lips, likened to a tart effect, which is reflected by a more swollen and more fleshy visual appearance of the lips.

According to one particular embodiment, the aqueous medium is the user's saliva.

According to another embodiment, the aqueous medium may be water applied by the user to the surface of the lips. This water or aqueous medium may be applied before, after or simultaneously with the organic acid and/or the carbonate or bicarbonate.

According to yet another embodiment, the aqueous medium may be directly combined with the acid and/or the carbonate.

According to a first embodiment, said organic acid and said carbonate or bicarbonate are placed in contact by superposition or by mixing at the time of their respective applications to the lips.

According to another embodiment, the organic acid and the carbonate or bicarbonate are mixed together extemporaneously before application of the mixture thus formed to the lips.

The two compositions comprising respectively the organic acid and the carbonate or bicarbonate may be, independently of each other, in a fluid, pasty or solid form.

According to one particular embodiment, at least one of the compositions is solid.

According to one preferred embodiment variant, the two compositions are liquid.

According to another preferred embodiment, the two compositions are anhydrous.

Thus, the present invention is also directed toward a lip makeup product comprising a first anhydrous composition containing, in a physiologically acceptable medium, at least one water-soluble organic acid, and a second anhydrous composition that is different from the first composition, containing, in a physiologically acceptable medium, at least one alkali metal or alkaline-earth metal carbonate or bicarbonate, with at least one of the two compositions also comprising a dyestuff.

The invention is also directed toward a lip makeup product comprising a first composition containing, in a physiologically acceptable medium, at least one water-soluble organic acid, and a second composition that is different from the first composition, containing, in a physiologically acceptable medium, at least one alkali metal or alkaline-earth metal carbonate or bicarbonate, at least one of the two compositions also comprising at least 0.005% by weight of at least one dyestuff relative to its total weight.

More particularly, the dyestuff is present in the composition containing the carbonate or bicarbonate.

The term "physiologically acceptable medium" means a medium that is compatible with human keratin materials, i.e. the skin, the lips, the scalp, the eyelashes, the eyes, the nails and/or the hair.

The first and second compositions may be applied, without preference, simultaneously or successively.

According to one embodiment variant, the first and second compositions are mixed together extemporaneously before application.

In order to avoid any risk of premature reaction between the organic acid and the alkali metal or alkaline-earth metal carbonate or bicarbonate, the first and second compositions are conditioned separately of each other, but combined in a single packaging assembly.

Alternatively, each of the first and second compositions may be conditioned in different packaging assemblies.

The first and second compositions may especially be in the form of a lipstick wand, a lip balm or a gloss.

A subject of the present invention is also an assembly for packaging and distributing compositions forming a product according to the invention, said assembly comprising at least two independent compartments comprising, respectively, each of said compositions and means for allowing the two compositions to be placed in contact in the form of a mixture or otherwise.

According to one embodiment variant, the mixing of the compositions is performed within said assembly just before use and thus before application to the lips.

According to another embodiment variant, the mixing of the two compositions is performed extemporaneously, either on a support such as, for example, cotton wool, or directly on the lips.

Organic Acid

Among the organic acids that may be used in the process according to the invention, any organic acid that is compatible with topical cosmetic use, especially $C_2$ to $C_{22}$ carboxylic acids, will be chosen. The acid in accordance with the invention should be water-soluble.

As examples of organic acids that are suitable in the context of the present invention, mention may be made especially of citric acid, tartaric acid, ascorbic acid, succinic acid, malic acid, malonic acid, fumaric acid, glutaric acid, adipic acid, pimelic acid, maleic acid, phthalic acid, glutamic acid, aspartic acid, glycolic acid, tartronic acid, hydroxybenzoic acid, salicylic acid, tropic acid, cinnamic acid, phenylacetic acid, nicotinic acid, sorbic acid and trimellitic acid, and mixtures thereof.

According to one preferred embodiment, the organic acid is citric acid.

Advantageously, the choice and amount of organic acid in the composition intended for application to the lips are adjusted to have a bubbly effect on the lips on contact with saliva. This amount may range from 0.5% to 15% and in particular from 0.5% to 9% by weight relative to the total weight of said composition.

Carbonate/Bicarbonate

The alkali metal or alkaline-earth metal carbonate or bicarbonate is chosen for its reactivity with regard to the associated organic acid. Its choice clearly falls within the competence of a person skilled in the art.

Among the examples of carbonate or bicarbonate compounds that may be used in the context of the present invention, mention may be made especially of sodium carbonate, sodium bicarbonate, potassium carbonate, potassium bicarbonate, magnesium carbonate, magnesium bicarbonate, calcium carbonate and calcium bicarbonate, and mixtures thereof.

Sodium bicarbonate is most particularly suitable for use in the invention.

Its amount is also adjusted with regard to that of the associated organic acid. It may especially range from 1% to 15% and in particular from 2% to 8% of the weight of the composition containing it.

According to one particular embodiment, the mole ratio between the organic acid and the carbonate or bicarbonate ranges from 0.5 to 10, in particular from 1 to 8 and preferably from 1 to 7.

Aqueous Medium

As indicated previously, the effervescence reaction induced by placing an organic acid and a carbonate or bicarbonate in contact takes place in aqueous medium.

For the purposes of the invention, the term "aqueous medium" means any medium containing water molecules that are liable to react with said organic acid and said carbonate or bicarbonate.

They may be water molecules provided independently of the organic acid and of the carbonate or bicarbonate. Examples that may be mentioned include the user's saliva, or alternatively water applied by the user to the surface of the lips.

They may also be water molecules included in one or other of the compositions comprising the organic acid or the carbonate or bicarbonate. In this specific case, the effervescence reaction may be obtained by simple placing in contact of the two compositions, at least one of them comprising an aqueous phase, without the need for an external provision of water molecules.

Thus, according to one embodiment variant, at least one of the compositions comprising the organic acid or the carbonate or bicarbonate, and more particularly that containing the organic acid, comprises an aqueous phase.

Compositions

The compositions containing, respectively, the organic acid and the carbonate or bicarbonate may be in any galenical form conventionally used for application to the lips.

Thus, the compositions according to the invention may be more or less fluid and may have the appearance of a cream, an ointment, a milk, a lotion, a serum, a paste, a mousse or a gloss. They may also be in solid form, for example in the form of a cast stick.

According to one particular embodiment, the compositions according to the invention are in the form of a lipstick wand.

Besides the organic acid and the carbonate or bicarbonate, the compositions may contain other compounds, provided that these compounds are compatible with those of the composition and, moreover, are not of a nature to affect the manifestation of the expected effervescence reaction.

For example, according to one preferred embodiment variant, at least one of the two compositions and preferably both the compositions comprise(s) at least one fatty phase formed from at least one oil.

The term "oil" means a fatty substance that is liquid at room temperature (25° C.)

As oils that may be used in the composition of the invention, examples that may be mentioned include:

hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil and Shea butter oil;

synthetic esters and ethers, especially of fatty acids, for instance the oils of formulae $R^1COOR^2$ and $R^1OR^2$ in which $R^1$ and $R^2$ represent, independently of each other, a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate, isostearyl isostearate or isononyl isononanoate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate (Prisorine 3631);

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

silicone oils, for instance volatile or non-volatile polymethylsiloxanes (PDMSs) containing a linear or cyclic silicone chain, which are liquid or pasty at room temperature, especially cyclopolydimethylsiloxanes (cyclomethicones) such as cyclohexasiloxane and cyclopentasiloxane; polydimethylsiloxanes (or dimethicones) comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyltrimethylsiloxysilicates and polymethylphenylsiloxanes;

fatty alcohols containing from 8 to 26 carbon atoms, for instance cetyl alcohol, stearyl alcohol and a mixture thereof (cetylstearyl alcohol);

partially hydrocarbon-based and/or silicone-based fluoro oils, for instance those described in document JP-A-2 295 912;

and mixtures thereof.

The term "hydrocarbon-based oil" hereinabove means any oil mainly comprising carbon and hydrogen atoms, and possibly ester, ether, fluoro and/or alcohol groups.

According to one preferred embodiment of the invention, the compositions have a reduced content of volatile oil, or are even free of volatile oil.

This fatty phase, formed from one or more of the above-mentioned oils, where appropriate as a mixture with other fatty substances and lipophilic constituents, may be in the form of an emulsion. These emulsions may be of oil-in-water, water-in-oil or even multiple type. Advantageously, they are oil-in-water emulsions.

These emulsions generally contain at least one emulsifier chosen from amphoteric, anionic, cationic and nonionic emulsifiers, used alone or as a mixture. The emulsifiers are chosen in an appropriate manner according to the continuous phase of the emulsion to be obtained (W/O or O/W).

As emulsifiers that may be used for the preparation of the W/O emulsions, examples that may be mentioned include alkyl esters or ethers of sorbitan, of glycerol or of sugars; silicone surfactants, for instance dimethicone copolyols such as the mixture of cyclomethicone and of dimethicone copolyol, sold under the names DC 5225 C and DC 3225 C by the company Dow Corning, and alkyl dimethicone copolyols such as lauryl methicone copolyol sold under the name "Dow Corning 5200 Formulation Aid" by the company Dow Corning, cetyl dimethicone copolyol sold under the name Abil EM 90® by the company Goldschmidt, and the mixture of Polyglyceryl-4 isostearate/cetyl dimethicone copolyol/hexyl laurate sold under the name Abil WE 09® by the company Goldschmidt. One or more co-emulsifiers may also be added thereto, which may be chosen, advantageously, from the group comprising branched-chain fatty acid esters of polyol, and especially branched-chain fatty acid esters of glycerol and/or of sorbitan, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

As emulsifiers that may be used for the preparation of the O/W emulsions, examples that may be mentioned include nonionic emulsifiers such as oxyalkylenated (more particularly polyoxyethylenated) fatty acid esters of polyols, for example polyethylene glycol stearates, for instance PEG-100 stearate, PEG-50 stearate and PEG-40 stearate; and mixtures thereof such as the mixture of glyceryl monostearate and of polyethylene glycol stearate (100 EO) sold under the name Simulsol 165 by the company SEPPIC; oxyalkylenated fatty acid esters of sorbitan comprising, for example, from 20 to 100 EO, for instance those sold under the trade names Tween 20 or Tween 60 by the company Uniqema; oxyalkylenated (oxyethylenated and/or oxypropylenated) fatty alkyl ethers; sugar esters, for instance sucrose stearate; and mixtures thereof, for instance the mixture of glyceryl stearate and of PEG-100 stearate sold under the name Arlacel 165 by the company Uniqema.

Coemulsifiers may be added to these emulsifiers, for instance fatty alcohols containing from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol.

According to another embodiment, the compositions containing a fatty phase, especially as defined above, may be anhydrous.

For the purposes of the invention, an anhydrous composition contains less than 10% by weight of water, especially less than 4% and in particular less than 1% by weight of water.

The compositions of the invention may also contain adjuvants that are common in cosmetics or dermatology, such as hydrophilic or lipophilic gelling agents, hydrophilic or lipophilic active agents, preserving agents (for example phenoxyethanol and parabens), antioxidants, solvents, fragrances, fillers, UV-screening agents, bactericides, dyestuffs, pigments, salts and polymers. The amounts of these various adjuvants are those conventionally used in the field under consideration, for example from 0.01% to 20% of the total weight of the composition containing them.

According to one particular embodiment, at least one of the compositions according to the invention also comprises at least one dyestuff and/or one filler.

Needless to say, a person skilled in the art will take care to select the optional additives(s) to be added to the composition according to the invention and the amount thereof, such that the desired makeup effect is not, or is not substantially, adversely affected by the envisaged addition.

Dyestuffs

According to one embodiment, the compositions according to the invention may also contain at least one dyestuff chosen from lipophilic dyes, hydrophilic dyes, pigments, nacres and materials with a specific optical effect, and mixtures thereof.

This dyestuff may be present in a proportion of at least 0.005% by weight, especially from 0.01% to 50% by weight relative to the total weight of the composition, in particular from 0.5% to 40% by weight, more particularly from 5% to 25%, especially from 0.01% to 20% and in particular from 0.1% to 10%, or even from 2% to 5% by weight, relative to the total weight of the composition containing them.

The term "pigments" should be understood as meaning white or colored, mineral or organic particles, which are insoluble in an aqueous solution and which are intended to color and/or opacify the resulting film.

The pigments may be present in a proportion of from 0.01% to 20% by weight, especially from 0.01% to 5% by weight and in particular from 0.02% to 7% by weight relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

They may also be pigments with a structure that may be, for example, of sericite/brown iron oxide/titanium dioxide/silica type. Such a pigment is sold, for example, under the reference Coverleaf® NS or JS by the company Chemicals and Catalysts, and has a contrast ratio in the region of 30.

The dyestuff may also comprise a pigment with a structure that may be, for example, of silica microsphere type containing iron oxide. An example of a pigment having this structure is the product sold by the company Miyoshi under the reference PC Ball® PC-LL-100 P, this pigment consisting of silica microspheres containing yellow iron oxide.

Among the organic pigments that may be used in the invention, mention may be made of carbon black, pigments of D&C type, lakes based on cochineal carmine or on barium, strontium, calcium or aluminum, or alternatively the diketopyrrolopyrroles (DPP) described in documents EP-A-542 669, EP-A-787 730, EP-A-787 731 and WO-A-96/08537.

According to one preferred variant, the composition containing the organic acid is free of pigments.

The term "nacres" should be understood as meaning iridescent or non-iridescent colored particles of any form, especially produced by certain molluscs in their shell, or else synthesized, and which have a color effect by optical interference.

The nacres may be chosen from nacreous pigments such as titanium mica coated with an iron oxide, mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the mica-based nacres Timica®, Flamenco® and Duochrome® sold by the company Engelhard, the Timiron® nacres sold by the company Merck, the Prestige® mica-based nacres, sold by the company Eckart, and the Sunshine® synthetic mica-based nacres, sold by the company Sun Chemical.

The nacres may more particularly have a yellow, pink, red, bronze, orangey, brown, gold and/or coppery color or tint.

The cosmetic compositions according to the invention may also comprise water-soluble or liposoluble dyes in a content ranging from 0.01% to 10% by weight and especially ranging from 0.01% to 5% by weight relative to the total weight of the cosmetic composition.

The liposoluble dyes are, for example, Sudan red, DC Red 17, DC Green 6, β-carotene, soybean oil, Sudan brown, DC Yellow 11, DC Violet 2, DC Orange 5 and quinoline yellow.

When the cosmetic compositions according to the invention comprise a water-soluble dye, this dye may be present in the composition in dispersed form.

The cosmetic composition according to the invention may also contain at least one material with a specific optical effect.

This effect is different from a simple conventional hue effect, i.e. a unified and stabilized effect as produced by standard dyestuffs, for instance monochromatic pigments. For the purposes of the invention, the term "stabilized" means lacking an effect of variability of the color as a function of the angle of observation or alternatively in response to a temperature change.

For example, this material may be chosen from particles with a metallic tint, goniochromatic coloring agents, diffracting pigments, thermochromic agents, optical brighteners, and also fibers, especially interference fibers. Needless to say, these various materials may be combined so as to simultaneously afford two effects, or even a novel effect in accordance with the invention.

The particles with a metallic tint that may be used in the invention are chosen in particular from:
  particles of at least one metal and/or of at least one metal derivative,
  particles comprising a mono-material or multi-material organic or mineral substrate, at least partially coated with at least one coat with a metallic tint comprising at least one metal and/or at least one metal derivative, and
  mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

As illustrations of these particles, mention may be made of aluminum particles, such as those sold under the names Starbrite 1200 EAC® by the company Siberline, and Metalure® by the company Eckart.

Mention may also be made of copper metal powders or alloy mixtures such as the reference 2844 sold by the company Radium Bronze, metallic pigments such as aluminum or bronze, such as those sold under the name Rotosafe® 700 from the company Eckart, the silica-coated aluminum particles sold under the name Visionaire Bright Silver® from the company Eckart and metal alloy particles, for instance the silica-coated bronze (alloy of copper and zinc) powders sold under the name Visionaire Bright Natural Gold® from the company Eckart.

They may also be particles comprising a glass substrate, such as those sold by the company Nippon Sheet Glass under the name Microglass Metashine®.

The goniochromatic coloring agent may be chosen, for example, from multilayer interference structures and liquid-crystal coloring agents.

Examples of symmetrical multilayer interference structures that may be used in the compositions prepared in accordance with the invention are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica$-$oxide/SiO_2/MoS_2$; $Fe_2O_3/SiO_2/mica$-$oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$;

SnO/mica/TiO$_2$/SiO$_2$/TiO$_2$/mica/SnO, pigments having these structures being sold under the name Xirona® by the company Merck (Darmstadt). By way of example, these pigments may be the pigments of silica/titanium oxide/tin oxide structure sold under the name Xirona Magic® by the company Merck, the pigments of silica/brown iron oxide structure sold under the name Xirona Indian Summer® by the company Merck and the pigments of silica/titanium oxide/mica/tin oxide structure sold under the name Xirona Caribbean Blue® by the company Merck. Mention may also be made of the Infinite Colors® pigments from the company Shiseido. Depending on the thickness and the nature of the various layers, different effects are obtained. Thus, with the Fe$_2$O$_3$/SiO$_2$/Al/SiO$_2$/Fe$_2$O$_3$ structure, the color changes from green-golden to red-grey for SiO$_2$ layers of 320 to 350 nm; from red to golden for SiO$_2$ layers of 380 to 400 nm; from violet to green for SiO$_2$ layers of 410 to 420 nm; from copper to red for SiO$_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix and also the products sold under the name Helicone® HC by the company Wacker.

Fillers

Among the fillers that may be used in the compositions of the invention, examples that may be mentioned include silica powder; talc; polyamide particles and especially those sold under the name Orgasol by the company Atochem; polyethylene powders; powders of natural organic materials such as starch powders, especially of crosslinked or non-crosslinked corn starch, wheat starch or rice starch, such as powders of starch crosslinked with octenylsuccinate anhydride, sold under the name Dry-Flo by the company National Starch; microspheres based on acrylic copolymers, such as those made of ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; and mixtures thereof. These fillers may be present in amounts ranging from 0 to 20% by weight and preferably from 1% to 10% by weight relative to the total weight of the composition containing them.

Active Agents

Examples of active agents that may be mentioned include:
moisturizers, for instance sodium lactate; polyols, and in particular glycerol, sorbitol and polyethylene glycols; mannitol; amino acids; hyaluronic acid; lanolin; urea and mixtures containing urea, such as NMF (Natural Moisturizing Factor); petroleum jelly; N-lauroylpyrrolidonecarboxylic acid and its salts; essential fatty acids; essential oils; hydroxyalkyl ureas such as N-(2-hydroxyethyl)urea sold under the name Hydrovance by the company National Starch; and mixtures thereof;
antiaging and antiwrinkle active agents, more particularly α-hydroxy acids and especially acids derived from fruit, for instance glycolic acid, lactic acid, malic acid, citric acid, tartaric acid and mandelic acid, derivatives thereof, and mixtures thereof; β-hydroxy acids, for instance salicylic acid and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate and magnesium or sodium ascorbyl phosphate; its esters, for instance ascorbyl acetate, ascorbyl palmitate and ascorbyl propionate, or its sugars, for instance glycosylated ascorbic acid, and mixtures thereof; β-keto acids; retinoids, for instance retinol (vitamin A) and its esters, retinal, retinoic acid and its derivatives, and also the retinoids described in documents FR-A-2 570 377, EP-A-199 636, EP-A-325 540 and EP-A-402 072; adapalene; carotenoids; C-glycoside derivative, for instance C-β-D-xylopyranoside-n-propan-2-one, especially C-β-D-xylopyranoside-n-propan-2-one in the form of a solution containing 30% active material in a water/propylene glycol mixture (60%/40% by weight) manufactured by the company Chimex under the trade name Mexoryl SBB®;
vitamins, for instance vitamins A and C mentioned above, and also vitamin E (tocopherol) and its derivatives; vitamin B3 (or vitamin PP or niacinamide) and its derivatives; vitamin B5 (or panthenol in its various forms: D-panthenol, DL-panthenol), and derivatives and analogues thereof, such as calcium panthotenate, panthetine, pantotheine, ethyl panthenyl ether, pangamic acid, pyridoxine, pantoyl lactose and natural compounds containing it such as royal jelly; vitamin D and its analogues such as those described in document WO-A-00/26167; vitamin F or its analogues such as mixtures of unsaturated acids containing at least one double bond and especially mixtures of linoleic acid, of linolenic acid and of arachidonic acid, or compounds containing them.

According to one particular embodiment, at least one of the compositions according to the invention also comprises at least one hydrophilic or lipophilic active agent.

The example that follows serves to illustrate the invention without, however, being limiting in nature. The amounts indicated are weight percentages of starting material, unless otherwise mentioned.

EXAMPLE 1

Preparation of a Lipstick Wand According to the Invention

| Ingredients | Composition 1 | Composition 2 | Composition 3 | Composition 4 |
|---|---|---|---|---|
| OILY PHASE | | | | |
| Tridecyl trimellitate | 38.36% | 37.71% | 40.31% | 37.67% |
| C$_{18-36}$ acid triglyceride | 11.39% | 11.20% | 11.97% | 11.19% |
| Bis(diglyceryl) poly(2-acyladipate) | 9.26% | 9.10% | 9.73% | 9.10% |
| Polybutene | 30% | 30% | 30% | 30% |
| PRESERVING AGENTS | 0.34% | 0.34% | 0.34% | 0.34% |
| DYESTUFF | | | | |
| Red 28 Lake | — | — | — | 0.05% |
| FILLER | | | | |
| Silica dimethyl silylate | 7% | 7% | 7% | 7% |
| FRAGRANCE | 0.50% | 0.50% | 0.50% | 0.5% |
| Sodium saccharinate | 0.15% | 0.15% | 0.15% | 0.15% |
| ACID/BICARBONATE | | | | |
| Citric acid | 3% | — | — | — |
| Sodium bicarbonate | — | 4% | — | 4% |

Procedure:

The oily phase is prepared by mixing together all the oils, at elevated temperature (about 80° C.). The fillers, pigments, acid, bicarbonate and active agents, when they are present, are then ground into the oily phase. The rest of the liposoluble ingredients are mixed at a temperature of about 80° C. into the ground material obtained previously. The gelling agents are dispersed with mechanical stirring of Rayneri type. Finally, the nacres and the lipodispersible active agents are added, and the paste obtained is conditioned in a tube.

Cosmetic Result:

In order to demonstrate the bubbly effect associated with the effervescence reaction when a lipstick composition according to the invention is applied, various individuals tested the four compositions above, applied in pairs according to the following combinations: 1+2, 1+3, 1+4, 2+3 and 2+4.

After application of each of these combinations, the film obtained on the surface of the lips was moistened so as to allow the effervescence reaction when citric acid and sodium bicarbonate are present.

The results obtained are as follows:
- when compositions 1 and 2 or compositions 1 and 4 comprising, respectively, citric acid (1) and sodium bicarbonate (2+4) are applied, moistening with saliva of the film obtained induces the expected effervescence reaction, which is manifested by a bubbly effect on the lips and also by slight tingling, reflected by a more swollen and more fleshy appearance of the lips;
- on the other hand, when composition 1 or 2 is applied with composition 3 containing neither citric acid nor sodium bicarbonate, or composition 2 with composition 4, both containing only sodium bicarbonate, moistening of the film obtained does not produce any effervescence reaction and consequently no bubbly effect on the lips, or any tingling sensation.

The invention claimed is:

1. A process of applying makeup to the lips, comprising at least one step of placing in contact on the surface of said lips comprising:
   a first anhydrous composition containing at least one water-soluble organic acid,
   a second anhydrous composition that is different from the first containing at least one alkali metal carbonate, alkali metal bicarbonate, alkaline-earth metal bicarbonate, or alkaline-earth metal carbonate, and
   an aqueous medium separate from the first anhydrous composition and the second anhydrous composition.

2. The process as claimed in claim 1, wherein the water-soluble organic acid and the alkali metal carbonate, alkali metal bicarbonate, alkaline-earth metal bicarbonate, or alkaline-earth metal carbonate are placed in contact by superposition or by mixing at the time of their respective applications to the lips.

3. The process as claimed in claim 1, wherein the water-soluble organic acid and the alkali metal carbonate, alkali metal bicarbonate, alkaline-earth metal bicarbonate, or alkaline-earth metal carbonate are mixed together extemporaneously before application of the mixture thus formed to the lips.

4. The process as claimed in claim 1, wherein the water-soluble organic acid is a carboxylic acid selected from the group consisting of citric acid, tartaric acid, ascorbic acid, succinic acid, malic acid, malonic acid, fumaric acid, glutaric acid, adipic acid, pimelic acid, maleic acid, phthalic acid, glutamic acid, aspartic acid, glycolic acid, tartronic acid, hydroxybenzoic acid, salicylic acid, tropic acid, cinnamic acid, phenylacetic acid, nicotinic acid, sorbic acid and trimellitic acid.

5. The process as claimed in claim 4, wherein the water-soluble organic acid is citric acid.

6. The process as claimed in claim 1, wherein the water-soluble organic acid is present in an amount ranging from 0.5% to 15% by weight relative to the total weight of the composition comprising it.

7. The process as claimed in claim 1, wherein the alkali metal bicarbonate is sodium bicarbonate.

8. The process as claimed in claim 7, wherein the sodium bicarbonate is present in an amount ranging from 1% to 15% by weight relative to the total weight of the composition comprising it.

9. The process as claimed in claim 1, wherein the mole ratio between the water-soluble organic acid and the alkali metal carbonate, alkali metal bicarbonate, alkaline-earth metal bicarbonate, or alkaline-earth metal carbonate ranges from 0.5 to 10.

10. The process as claimed in claim 1, wherein the compositions are conditioned separately of each other, but combined in a single packaging assembly.

11. The process as claimed in claim 1, wherein the compositions are conditioned separately of each other in different packaging assemblies.

12. The process as claimed in claim 1, wherein the compositions are in the form of a lipstick and/or gloss wand.

13. A product for applying makeup to the lips, comprising a first anhydrous composition containing, in a physiologically acceptable medium, at least one water-soluble organic acid, and a second anhydrous composition that is different from the first composition, containing, in a physiologically acceptable medium, at least one alkali metal carbonate, alkali metal bicarbonate, alkaline-earth metal bicarbonate, or alkaline-earth metal carbonate, with at least one of the two compositions also comprising a dyestuff.

14. The makeup product as claimed in claim 13, further comprising an aqueous medium separate from the first composition and the second composition.

15. An assembly for packaging and distributing compositions forming a product as claimed in claim 13 said assembly comprising at least:
   two independent compartments comprising, respectively, each of said compositions, and
   means for allowing the two compositions to be placed in contact.

16. The assembly as claimed in claim 15, wherein the means for placing the two compositions in contact are such that the mixing of said compositions is performed in said assembly just before application to the lips.

17. The assembly as claimed in claim 15, wherein the means for placing the two compositions in contact are such that the mixing of the two compositions is performed extemporaneously outside said assembly on a support or directly on the lips.

18. The process according to claim 1, wherein the aqueous medium is applied before or simultaneously with said water-soluble organic acid and/or said alkali metal carbonate, alkali metal, bicarbonate, alkaline-earth metal bicarbonate, or alkaline-earth metal carbonate.

19. The process according to claim 1, wherein the aqueous medium is applied after or simultaneously with said water-soluble organic acid and/or said alkali, metal carbonate, alkali metal bicarbonate, alkaline-earth metal bicarbonate, or alkaline-earth metal carbonate.

* * * * *